(12) United States Patent
Haemmerle et al.

(10) Patent No.: US 8,288,101 B2
(45) Date of Patent: Oct. 16, 2012

(54) METHOD FOR THE SPECIFIC DETECTION OF LOW ABUNDANCE RNA SPECIES IN A BIOLOGICAL SAMPLE

(75) Inventors: Thomas Haemmerle, Vienna (AT); Carsten Urban, Vienna (AT); Franz Gruber, Vienna (AT)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 183 days.

(21) Appl. No.: 12/617,063

(22) Filed: Nov. 12, 2009

(65) Prior Publication Data

US 2010/0124748 A1    May 20, 2010

Related U.S. Application Data

(60) Provisional application No. 61/114,858, filed on Nov. 14, 2008.

(51) Int. Cl.
*C12Q 1/68* (2006.01)
*C12P 19/34* (2006.01)

(52) U.S. Cl. ............... 435/6.12; 435/6.1; 435/6.11

(58) Field of Classification Search ............ None
See application file for complete search history.

(56) References Cited

U.S. PATENT DOCUMENTS

| | | | |
|---|---|---|---|
| 2005/0250112 A1* | 11/2005 | Padmabandu et al. | 435/6 |
| 2006/0024799 A1 | 2/2006 | Shannon | |
| 2006/0257871 A1* | 11/2006 | Chaubron et al. | 435/6 |

FOREIGN PATENT DOCUMENTS

| | | | |
|---|---|---|---|
| EP | 0 669 401 B1 | * | 12/2001 |
| EP | 1 477 561 A2 | | 11/2004 |
| WO | WO 9511923 A1 | * | 5/1995 |
| WO | 00/17391 A1 | | 3/2000 |

OTHER PUBLICATIONS

Bustin, S.A., "Absolute quantification of mRNA using real-time reverse transcription polymerase chain reaction assays," Journal of Molecular Endocrinology, 2000, vol. 25, pp. 169-193.*

Chandler et al., "Reverse Transcriptase (RT) Inhibition of PCR at Low Concentrations of Template and Its Implications for Quantitative RT-PCR," Applied and Environmental Microbiology, 1998, vol. 64, No. 2, p. 669-677.*

Grondahl et al., "Rapid Identification of Nine Microorganisms Causing Acute Respiratory Tract Infections by Single-Tube Multiplex Reverse Transcription-PCR: Feasibility Study," Journal of Microbiology, 1999, vol. 37, No. 1, pp. 1-7.*

Marios, C., et al., "A reverse transcription-PCR assay to detect viable *Mycoplasma synoviae* in poultry environmental samples," *Veterinary Microbiology*, vol. 89(1), pp. 17-28 (Oct. 2, 2002).

Stankovic, K., et al., "Real-time quantitative RT-PCR for low-abundance transcripts in the inner ear: analysis of neurotrophic factor expression," *Hearing Research*, vol. 185(1-2), pp. 97-108 (Nov. 2003).

* cited by examiner

*Primary Examiner* — Young J Kim
(74) *Attorney, Agent, or Firm* — Kilpatrick Townsend & Stockton LLP

(57) ABSTRACT

The present invention relates to a method and a kit for the detection of low abundance RNA species in a biological sample and to a method and a kit for the detection of a *mycoplasma* contamination in a biological sample.

14 Claims, No Drawings

METHOD FOR THE SPECIFIC DETECTION OF LOW ABUNDANCE RNA SPECIES IN A BIOLOGICAL SAMPLE

CROSS-REFERENCE TO RELATED APPLICATIONS

This application claims the benefit of U.S. Provisional Application No. 61/114,858, filed Nov. 14, 2008, which application is herein incorporated by reference.

FIELD OF THE INVENTION

The present invention relates to a method and a kit for the detection of low abundance RNA species in a biological sample and to a method and a kit for the detection of a *mycoplasma* contamination in a biological sample.

BACKGROUND OF THE INVENTION

Among the most wide-spread and successful methods for the detection and analysis of RNA molecules is the so-called RT/PCR (reverse transcription/polymerase chain reaction). In this method, RNA molecules are transcribed into cDNA molecules by a reverse transcriptase (RT) and are then detected and/or analyzed by PCR-based methods.

Early researchers in this field have used either avian myeloblastosis virus RT or Moloney murine leukemia virus RT for reverse transcription. However, a significant problem in using RNA as a template for cDNA synthesis was the inability of these mesophilic viral RTs to synthesize cDNA through stable RNA secondary structures. To circumvent this problem, reverse transcription can be performed at increased reaction temperatures which can resolve secondary RNA structures, and additionally increase the specificity of primer extension. This requires the use of thermostable enzymes for reverse transcription, like *Thermus thermophilus* DNA polymerase (Tth pol) which is active at a temperature optimum of 70° C.

However, the use of thermostable enzymes for reverse transcription also generates new problems. In particular, when trying to detect and/or analyze low abundance RNA species in a biological sample, the thermostable enzyme for reverse transcription can catalyze the generation of non-specific reaction products during subsequent RT/PCR steps. This is especially the case in samples that have a large background of total RNA, and results in a substantial increase of the limit of detection of the target RNA to levels far above what can be necessary, for example in the quality control of biopharmaceutical products. To circumvent this problem, all handling and RT/PCR steps subsequent to reverse transcription have to be performed at elevated temperatures and under hotstart conditions. This, however, is often impractical and disadvantageous, especially when working in industrial scales.

An application wherein sensitive detection of low abundance RNA species, often in a large background of total RNA, is of particular relevance is the detection of a *mycoplasma* contamination in a biological sample.

Mycoplasmas are bacterial microorganisms with one of the smallest known genomes able to self-replicate. While most *mycoplasmas* are naturally harmless commensals, some of them are able to infect their natural hosts and cause diseases of varying severity. Mycoplasmas, particularly species of the genera *Mycoplasma* and *Acholeplasma*, are also frequent causes of contamination of primary and continuous cell lines and represent a serious problem for research and industrial laboratories involved in the development and production of cell-derived biological and pharmaceutical products. Thus, in spite of all preventive measures usually employed during the process of cell line propagation and handling, *mycoplasma* contamination continues to be a frequently occurring problem.

The analytical protocols recommended for *mycoplasma* testing of cell lines and cell-derived biological products include the use of broth/agar culture and indicator cell line tests. The broth/agar culture method is aimed at the detection of cultivable mycoplasmal agents, while the indicator cell line is used to detect fastidious non-cultivable *mycoplasma* species. Although the combination of these two methods enables efficient *mycoplasma* detection, the overall testing procedures are expensive, laborious and time-consuming (a minimum of 28 days). Moreover, there exists a number of non-cultivable *mycoplasma* species that are not amenable to this approach.

Novel *mycoplasma* testing methods based on the amplification of nucleic acids, in particular of *mycoplasma* derived ribosomal RNA have recently been developed. These methods have certain advantages with respect to costs, analytical sensitivity, simplicity and time. However, the detection limit of currently available methods is still above what is necessary in the quality control of biopharmaceutical products, especially when working with samples that have a large background of total RNA or other macromolecules.

Therefore, a need exists in the field to improve current RT/PCR methods to allow for improved detection limits of low abundance RNA species in biological samples.

The solution to the above problem is achieved by the embodiments characterized in the claims.

SUMMARY OF THE INVENTION

It is an object of the present invention to provide an improved method for the detection of low abundance RNA species in a biological sample. In particular, the present invention relates to said method and a kit for the detection of low abundance RNA species in a biological sample. Further, it is another object of the present invention to provide an improved method and a kit for the detection of a *mycoplasma* contamination in a sample.

DETAILED DESCRIPTION OF THE INVENTION

In one aspect, the present invention relates to a method for the detection of low abundance target RNA species in a biological sample, comprising the steps of:
(a) reverse transcription of RNA into cDNA using a reverse transcriptase (RT);
(b) inactivation of the RT; and
(c) detection of the target cDNA by polymerase chain reaction (PCR).

The term "biological sample" as used herein relates to any sample containing or suspected of containing biologically relevant macromolecules, like e.g. samples originating from various stages of the production process of biopharmaceutical products, e.g. vaccines or recombinant proteins, cell culture supernatants, cell lysates, cell extracts, food or environmental samples, samples originating from the human or animal body, like whole blood, serum, plasma, urine, liquor or smears, any other samples of biological origin and any other composition that contains or is suspected of containing RNA.

In a preferred embodiment of the present invention, the biological sample has a large background of cellular components.

The term "cellular components" as used herein relates to cell organelles, proteins, peptides, membranes, lipids, nucleic acids, in particular non-target RNA species, and combinations or fragments thereof.

In another preferred embodiment of the present invention, the biological sample has a large background of total RNA.

The term "large background of total RNA" as used herein relates to a situation wherein the target RNA is present as less than one molecule in $10^4$ total RNA molecules, preferably as less than one molecule in $10^6$ total RNA molecules, more preferably as less than one molecule in $10^8$ total RNA molecules, and most preferably as less than one molecule in $10^{10}$ total RNA molecules.

In a preferred embodiment of the present invention, the target RNA is present in an amount of less than 10000 copies per ml of sample, preferably less than 1000 copies per ml of sample, more preferably less than 100 copies per ml of sample, and most preferably less than 10 copies per ml of sample.

According to a preferred embodiment of the present invention, the reverse transcription of RNA into cDNA using a RT according to the method of the present invention is performed under hotstart conditions.

The term "hotstart conditions" as used herein relates to any conditions wherein the reaction mixture is heated to or above the melting temperature of the primer/nucleic acid complex prior to the addition of the enzyme that is responsible for primer elongation, or wherein the enzyme that is responsible for primer elongation is inactive at ambient temperature and is activated by a high-temperature activation step that is performed at or above the melting temperature of the primer/nucleic acid complex.

In a preferred embodiment of the present invention, the method of the present invention further comprises after the reverse transcription of RNA into cDNA using a RT a step of amplifying the target cDNA using the same RT. This further step is called "prime PCR" and is preferably performed for 5 to 15 cycles at hotstart conditions, more preferably for 5 to 11 cycles at hotstart conditions, and most preferably for 5 or for 10 cycles at hotstart conditions.

Accordingly, in another aspect, the present invention relates to a method for the detection of low abundance RNA species in a biological sample, comprising the steps of:
(a) reverse transcription of RNA into cDNA using a reverse transcriptase (RT);
(b) amplification of cDNA by polymerase chain reaction (PCR) using the RT of step (a);
(c) inactivation of the RT; and
(d) detection of the target cDNA by PCR.

Enzymes that have both RT (i.e. RNA-dependent DNA polymerase) and DNA polymerase (i.e. DNA-dependent DNA polymerase) activity are well known in the art and include e.g. *Thermus thermophilus* DNA polymerase (Tth pol). The conditions under which a certain enzyme exhibits a certain activity are also well known in the art. In the case of Tth pol, reverse transcriptase activity is promoted by $Mn^{2+}$ ions and DNA polymerase activity by $Mg^{2+}$ ions.

In a preferred embodiment of the present invention, the RT used in the method of the present invention is *Thermus thermophilus* DNA polymerase (Tth pol). In a further preferred embodiment, the Tth pol is produced recombinantly (rTth-pol).

In another preferred embodiment of the present invention, the RT is inactivated in the method of the present invention, preferably by a method selected from the group, consisting of heat treatment, treatment with phenol, treatment with proteinase K, and treatment with a chaotropic agent.

Heat treatment according to the present invention comprises heating the reaction mixture containing the RT to 80 to 100° C., preferably to 90 to 100° C., more preferably to 95° C. Duration of the heat treatment is 15 to 90 minutes, preferably 30 to 75 minutes, more preferably 60 minutes. In an especially preferred embodiment, heat treatment comprises heating the reaction mixture containing the RT to 95° C. for 60 minutes.

Treatment with proteinase K according to the present invention comprises the addition of 1 to 10 units of proteinase K to the reaction mixture, more preferably 2 to 5 units of proteinase K, or most preferably 5 units of proteinase K. Duration of the proteinase K treatment is 30 to 90 minutes, preferably 45 to 75 minutes, or most preferably 60 minutes. In an especially preferred embodiment, treatment with proteinase K comprises the addition of 5 units of proteinase K for 60 minutes.

In a preferred embodiment of the present invention, the RT is inactivated in the method of the present invention by treatment with a chaotropic agent. Treatment with a chaotropic agent according to the present invention comprises the addition of a chaotropic agent to the reaction mixture containing the RT in an amount and for a time that is sufficient to inactivate the RT. Amounts and times of a particular chaotropic agent are well known in the art. In a more preferred embodiment of the present invention, the chaotropic agent is selected from the group, consisting of urea, lithium perchlorate and a guanidinium salt. In a most preferred embodiment, the chaotropic agent is a guanidinium salt.

In a further preferred embodiment of the present invention, the method of the present invention further comprises after inactivation of the RT using a chaotropic agent a step of removing the chaotropic agent from the reaction mixture. Methods to remove the chaotropic agent from the reaction mixture are well known in the art and include for example the purification of the nucleic acids contained in the reaction mixture using DNA-binding spin columns.

The detection of the target cDNA by PCR is also called "boost PCR". In a preferred embodiment of the present invention, the polymerase chain reaction (PCR) in the method of the present invention is a real-time PCR.

The term "real-time PCR" as used herein relate to any method that is based on the polymerase chain reaction (PCR) and allows to amplify and simultaneously quantify a targeted DNA molecule.

In a preferred embodiment of the present invention, the target RNA is derived from a *mycoplasma*. The term "*mycoplasma*" as used herein relates to any member of the class Mollicutes which includes the genera *Mycoplasma, Ureaplasma, Mesoplasma, Entomoplasma, Spiroplasma, Acholeplasma, Asteroleplasma,* and *Thermoplasma*. In a more preferred embodiment of the present invention, the *mycoplasma* is selected from the group, consisting of *Acholeplasma laidlawii, Mycoplasma gallisepticum, Mycoplasma hyorhinis, Mycoplasma hominis, Mycoplasma fermentans, Mycoplasma synoviae,* and *Mycoplasma orale*.

In a further preferred embodiment of the present invention, the target RNA is 16S ribosomal RNA (16S rRNA).

In another aspect, the present invention relates to a method for the detection of a *mycoplasma* contamination in a biological sample, comprising the steps of:
(a) extraction of total RNA from the sample;
(b) reverse transcription of RNA into cDNA using a reverse transcriptase (RT);
(c) amplification of cDNA derived from *mycoplasma* 16S ribosomal RNA (16S rRNA) by polymerase chain reaction (PCR) using the RT of step (b);

(d) inactivation of the RT by addition of a chaotropic agent;
(e) removal of the chaotropic agent from the reaction mixture; and
(f) detection of cDNA derived from *mycoplasma* 16S rRNA by polymerase chain reaction (PCR).

Means for the extraction of total RNA from a sample are well known in the art and include extraction with phenol/chloroform and precipitation with isopropanol.

In a preferred embodiment of the present invention, the *mycoplasma* contamination to be detected is a contamination of not more than about 10 cfu/ml *mycoplasma* in the sample.

Primers for the reverse transcription of *mycoplasma* 16S rRNA, as well as primers for the amplification of cDNA derived from *mycoplasma* 16S rRNA by PCR are well known in the art.

In a preferred embodiment of the present invention, the reverse transcription of RNA into cDNA using a RT of the method for the detection of a *mycoplasma* contamination in a sample is performed under hotstart conditions.

In another preferred embodiment of the present invention, the RT used in the method for the detection of a *mycoplasma* contamination in a sample is *Thermus thermophilus* DNA polymerase (Tth pol). In a further preferred embodiment, the Tth pol is produced recombinantly (rTth-pol).

In a further preferred embodiment of the present invention, the chaotropic agent used in the method for the detection of a *mycoplasma* contamination in a sample is selected from the group, consisting of urea, lithium perchlorate and a guanidinium salt. In a most preferred embodiment, the chaotropic agent is a guanidinium salt.

In one further preferred embodiment of the present invention, the PCR in the method for the detection of *mycoplasma* contamination in a sample is a real-time PCR.

In another aspect, the present invention relates to a kit for the detection of low abundance target RNA species in a biological sample, comprising at least a RT and means for the inactivation of the RT. Means for the inactivation of the RT may be proteinase K or a chaotropic agent. The kit may further comprise e.g. primers for the reverse transcription, primers for the detection of specific cDNAs, carrier RNAs, calibrator RNA, calibrator DNA, suitable enzymes, buffers, reagents, reaction containers and consumables.

In a further aspect, the present invention relates to a kit for the detection of a *mycoplasma* contamination in a biological sample, comprising at least a recombinant *Thermus thermophilus* DNA polymerase (rTth-pol), suitable primers for the reverse transcription of *mycoplasma* 16S rRNA, suitable primers for the amplification of cDNA derived from *mycoplasma* 16S rRNA, a chaotropic agent for the inactivation of the rTth-pol, means for removing the chaotropic agent from the reaction mixture, and primers for the detection of cDNA derived from *mycoplasma* 16S rRNA by PCR, e.g. real-time PCR. Means for removing the chaotropic agent may be DNA-binding spin columns. The kit may further comprise e.g. means for extracting total RNA from a sample, carrier RNAs, calibrator RNA, calibrator DNA, suitable enzymes, buffers, reagents, reaction containers and/or consumables. Means for extracting total RNA may be phenol, chloroform and isopropanol, or buffers containing the same.

The present invention will be further illustrated in the following examples without any limitation thereto.

EXAMPLES

General Procedure

The method starts with the centrifugation of the biological sample of interest followed by the extraction of total RNA from the sample pellet. RNA is then reverse transcribed into cDNA using recombinant *Thermus thermophilus* DNA polymerase (rTth-pol) in the presence of $Mn^{2+}$ at hotstart conditions. After chelation of $Mn^{2+}$ and addition of $Mg^{2+}$, the rTth-pol performs PCR amplification for 5 cycles or for 10 cycles at hotstart conditions (prime PCR). The PCR reaction is then transferred to a guanidine containing buffer to inactivate the rTth-pol. Purification with a spin-column based kit results in purified PCR products of the prime PCR which are then co-amplified with a DNA standard (calibrator DNA) in a duplex real-time PCR (boost PCR). Alternatively, a RNA standard (calibrator RNA) can be added at the beginning of RNA extraction to standardize and control the procedure from the beginning Experimental Procedures:

RNA extraction. All steps were performed in 2 ml reaction tubes. Two ml of the sample were centrifuged at 4° C. for 10 min at 1000 rpm. The pellet was resuspended in 1 ml RNA-Bee™ (Tel-Test Inc., TX), 5 µl of 1 mg/ml yeast tRNA were added and the sample incubated for 20 min in a centrifuge at 70° C. and 1000 rpm. Afterwards, 110 µl chloroform were added and the phases separated by centrifugation for 5 min at 13000 rpm. RNA was precipitated by addition of 500 µl isopropanol to the resulting upper phase and the samples were kept on dry ice for 5 min. The RNA pellet was collected by centrifugation for 15 min at 13000 rpm, washed with 500 µl 70% EtOH, and the sample was centrifuged for 10 min at 13000 rpm. The supernatant was discarded and the RNA pellet was dissolved in 250 µl bidest. $H_2O$ (bdH$_2$O).

Reverse transcription. 6 µl RT mix (1 µl 10× reverse transcription buffer (Applied Biosystems, Austria), 1 µl 10 mM $MnCl_2$, 0.5 µl 10 µM reverse primer, 0.8 µl 2.5 mM of each dNTP, 2.2 µl (5.5 U) rTth-pol and 0.5 µl bdH$_2$O) were added to 4 µl RNA extract. Reverse transcription was performed for 2 min at 80° C., 5 min at 62° C., 10 min at 70° C. and 2 min at 80° C.

Prime PCR. 40 µl PCR mix (4 µl 10× chelating buffer (Applied Biosystems, Austria), 5 µl 25 mM $MgCl_2$, 2.5 µl 10 µM forward primer, 2 µl 10 µM reverse primer and 26.5 µl bdH$_2$O) which was pre-heated to 85° C.±5° C. were added to the reaction mixture obtained from the reverse transcription. PCR was conducted according to the following protocol: 2 min at 80° C., 2 min at 95° C., 5×(10 sec at 95° C., 30 sec at 62° C., 30 sec at 72° C.).

Inactivation of RT. After the prime PCR, 50 µl of the still hot reaction mixture were added to 253 µl inactivation buffer (3 µl carrier RNA (1 µg/µl yeast tRNA), 250 µl buffer PBI (Qiaquick PCR Purification Kit; Qiagen, Germany)) and mixed. The samples were applied to a Qiaquick mini spin column (Qiagen, Germany) in a 2 ml collection tube and centrifuged for 1 min at 13000 rpm. The collection tube was discarded, the spin column placed in a fresh collection tube, 750 µl buffer PE (Qiaquick PCR Purification Kit; Qiagen, Germany) were added and the sample centrifuged for 1 min at 13000 rpm. Again the collection tube was discarded and the spin column centrifuged in a fresh collection tube for 1 min at 13000 rpm. The spin column was then placed in a fresh 1.5 ml reaction tube, 50 µl 10 mM Tris (pH 8.0) were added and the DNA eluted by centrifugation for 1 min at 13000 rpm.

Boost PCR. 10 µl of the eluted DNA were put in an optical tube, and 5 µl of calibrator DNA as a control and 35 µl TMPCR mix (1× TaqMan Buffer A (Applied Biosystems, Austria), 5 mM $MgCl_2$, 200 nM of each primer, 100 nM of each probe, 200 µM of each dNTP, 9% glycerol (wt/vol), 0.05% gelatin (wt/vol), 0.01% Tween 20 (wt/vol), 2.5 U AmpliTaq Gold Polymerase (Applied Biosystems, Austria))

were added. Real-time PCR was performed according to the following protocol: 10 min at 95° C., 40× (15 sec at 95° C., 1 min at 62° C.).

Example 1

Detection of *Mycoplasma synoviae* in Samples Originating from the Manufacturing Process of a Vaccine Samples originating from the manufacturing process of a vaccine were spiked with varying amounts of *Mycoplasma synoviae* and processed according to the above experimental procedures. To demonstrate the beneficial effect of RT inactivation (samples 1 to 6), control samples were included wherein RT was not inactivated (samples 7 to 12), or wherein no RT was added at all (samples 13 to 18). After RNA extraction, reverse transcription, prime PCR and RT inactivation, samples were analyzed for the presence of cDNA by real-time PCR. Before this boost PCR, a defined amount of calibrator DNA was added to the reaction mixture. This calibrator DNA was amplified together with the target nucleic acids using a different set of primers. Signals from calibrator and target DNA were differentiated by using different labeled probes. The primers for prime and boost PCR were specific for *mycoplasma* 16S rRNA. The results summarized in Table 1 show Ct values from the real-time PCR, i.e. the number of cycles needed to detect a specific PCR product. Lower Ct values mean more ready detection, whereas Ct values of 40 indicate that no product was detectable over the whole run of the real-time PCR.

TABLE 1

Detection of *Mycoplasma synoviae* in samples originating from the manufacturing process of a vaccine

| Sample # | M. synoviae [cfu/ml] | RT present | RT inactivated | Ct (calibrator) | Ct (target) |
|---|---|---|---|---|---|
| 1 | 100 | + | + | 29.88 | 30.82 |
| 2 | 100 | + | + | 29.67 | 30.71 |
| 3 | 10 | + | + | 29.68 | 33.16 |
| 4 | 10 | + | + | 29.71 | 35.42 |
| 5 | — | + | + | 29.85 | 40.00 |
| 6 | — | + | + | 29.95 | 40.00 |
| 7 | 100 | + | − | 39.30 | 40.00 |
| 8 | 100 | + | − | 34.41 | 40.00 |
| 9 | 10 | + | − | 34.64 | 40.00 |
| 10 | 10 | + | − | 35.12 | 40.00 |
| 11 | — | + | − | 34.42 | 40.00 |
| 12 | — | + | − | 36.11 | 40.00 |
| 13 | 100 | − | − | 29.56 | 40.00 |
| 14 | 100 | − | − | 29.43 | 40.00 |
| 15 | 10 | − | − | 29.39 | 40.00 |
| 16 | 10 | − | − | 29.40 | 40.00 |
| 17 | — | − | − | 29.31 | 40.00 |
| 18 | — | − | − | 29.37 | 40.00 |

The results in Table 1 clearly show that while the presence of active RT (samples 7 to 12) does not allow for the detection of even 100 cfu/ml *Mycoplasma synoviae*, inactivation of the RT allows for the detection of even as little as 10 cfu/ml. The increase of Ct values for the calibrator DNA in the samples without RT inactivation shows that without inactivation, the RT is able to catalyze reactions that lead to unspecific reaction products that interfere with the generation of specific products of calibrator and target DNA during boost PCR. This interpretation is supported by the fact that in the samples where no RT has been added at all (samples 13 to 18), the Ct values for the calibrator DNA are again at the same level as in the samples where RT was inactivated (samples 1 to 6).

Example 2

Detection of *Mycoplasma fermentans* in Samples Originating from the Manufacturing Process of a Vaccine The same samples as in Example 1 were spiked with varying amounts of Mycoplasma fermentans and processed according to the above experimental procedures. To demonstrate the beneficial effect of RT inactivation (samples 1 to 6), control samples were included wherein RT was not inactivated (samples 7 to 12). After RNA extraction, reverse transcription, prime PCR and RT inactivation, samples were analyzed for the presence of cDNA by real-time PCR. Before this boost PCR, a defined amount of calibrator DNA was added to the reaction mixture. The primers for prime and boost PCR were again specific for *mycoplasma* 16S rRNA. The results summarized in Table 2 show Ct values from the real-time PCR.

TABLE 2

Detection of *Mycoplasma fermentans* in samples originating from the manufacturing process of a vaccine

| Sample # | M. fermentans [cfu/ml] | RT present | RT inactivated | Ct (calibrator) | Ct (target) |
|---|---|---|---|---|---|
| 1 | 100 | + | + | 29.31 | 29.57 |
| 2 | 100 | + | + | 29.46 | 30.44 |
| 3 | 10 | + | + | 29.30 | 33.46 |
| 4 | 10 | + | + | 29.47 | 34.72 |
| 5 | — | + | + | 29.67 | 40.00 |
| 6 | — | + | + | 29.27 | 40.00 |
| 7 | 100 | + | − | 40.00 | 40.00 |
| 8 | 100 | + | − | 40.00 | 40.00 |
| 9 | 10 | + | − | 40.00 | 40.00 |
| 10 | 10 | + | − | 40.00 | 40.00 |
| 11 | — | + | − | 40.00 | 40.00 |
| 12 | — | + | − | 40.00 | 40.00 |

The results in Table 2 confirm that, while the presence of active RT (samples 7 to 12) does not allow for the detection of even 100 cfu/ml *Mycoplasma fermentans*, inactivation of the RT allows for the detection of even as little as 10 cfu/ml. The increase of Ct values for the calibrator DNA in the samples without RT inactivation again confirms that without inactivation, the RT is able to catalyze reactions that lead to unspecific reaction products that interfere with the generation of specific products of calibrator and target DNA during boost PCR.

Example 3

Detection of *Mycoplasma fermentans* in Samples Originating from the Manufacturing Process of a Recombinant Protein Samples originating from the manufacturing process of a recombinant protein were spiked with varying amounts of *Mycoplasma fermentans* and processed according to the above experimental procedures. The beneficial effect of RT inactivation is shown in table 3, samples 1 to 6. As for the samples derived from the manufacturing process of a vaccine, the procedure also allows the detection of as little as 10 cfu/ml *Mycoplasma fermentans* spiked into a suspension of cells used to manufacture a recombinant protein.

TABLE 3

Detection of *Mycoplasma fermentans* in samples originating from the manufacturing process of a recombinant protein

| Sample # | *M. fermentans* [cfu/ml] | RT present | RT inactivated | Ct (calibrator) | Ct (target) |
|---|---|---|---|---|---|
| 1 | 100 | + | + | 28.33 | 27.34 |
| 2 | 100 | + | + | 28.56 | 27.15 |
| 3 | 10 | + | + | 28.57 | 30.12 |
| 4 | 10 | + | + | 28.50 | 30.72 |
| 5 | — | + | + | 28.66 | 40.00 |
| 6 | — | + | + | 28.38 | 40.00 |

What is claimed is:

1. A method for the detection of low abundance target RNA species in a biological sample, comprising the steps of:
   (a) reverse transcription of RNA into cDNA using a reverse transcriptase (RT), wherein step (a) is performed under hotstart conditions;
   (b) inactivation of the RT; and
   (c) detection of the target cDNA by polymerase chain reaction (PCR),
   wherein the biological sample has a large background of cellular components and a large background of total RNA, and wherein the RT is a recombinant *Thermus thermophilus* DNA polymerase (rTth-pol).

2. The method of claim 1, further comprising after step (a) the step of amplifying the target cDNA using the RT of step (a).

3. The method of claim 1, wherein the RT is inactivated in step (b) by a method selected from the group consisting of heat treatment, treatment with phenol, treatment with proteinase K, and treatment with a chaotropic agent.

4. The method of claim 3, wherein the RT is inactivated by treatment with a chaotropic agent, further comprising after step (b) the step of removing the chaotropic agent.

5. The method of claim 4, wherein the chaotropic agent is selected from the group consisting of urea, lithium perchlorate, and a guanidinium salt.

6. The method of claim 1, wherein the polymerase chain reaction (PCR) of step (c) is a real-time PCR.

7. The method of claim 1, wherein the target RNA is derived from a mycoplasma.

8. The method of claim 7, wherein the *mycoplasma* is selected from the group, consisting of *Acholeplasma laidlawii, Mycoplasma gallisepticum, Mycoplasma hyorhinis, Mycoplasma hominis, Mycoplasma fermentans, Mycoplasma synoviae*, and *Mycoplasma orale*.

9. The method of claim 7, wherein the target RNA is 16S ribosomal RNA.

10. A method for the detection of a *mycoplasma* contamination in a biological sample, comprising the steps of:
    (a) extraction of total RNA from the biological sample;
    (b) reverse transcription of RNA into cDNA using a reverse transcriptase (RT);
    (c) amplification of cDNA derived from *mycoplasma* 16S ribosomal RNA (16S rRNA) by polymerase chain reaction (PCR) using the RT of step (b);
    (d) inactivation of the RT by addition of a chaotropic agent;
    (e) removal of the chaotropic agent from the reaction mixture; and
    (f) detection of cDNA derived from *mycoplasma* 16S rRNA by polymerase chain reaction (PCR),
    wherein the RT is a recombinant *Thermus thermnophilus* DNA polymerase (rTTh-pol).

11. The method of claim 10, wherein step (b) is performed under hotstart conditions.

12. The method of claim 10, wherein the chaotropic agent is selected from the group consisting of urea, lithium perchlorate, and a guanidinium salt.

13. The method of claim 10, wherein the polymerase chain reaction (PCR) of step (f) is a real-time PCR.

14. The method of claim 10, wherein the *mycoplasma* is selected from the group, consisting of *Acholeplasma laidlawii, Mycoplasma gallisepticum, Mycoplasma hyorhinis, Mycoplasma hominis, Mycoplasma fermentans, Mycoplasma synoviae*, and *Mycoplasma orale*.

* * * * *

UNITED STATES PATENT AND TRADEMARK OFFICE
CERTIFICATE OF CORRECTION

| | | |
|---|---|---|
| PATENT NO. | : 8,288,101 B2 | Page 1 of 1 |
| APPLICATION NO. | : 12/617063 | |
| DATED | : October 16, 2012 | |
| INVENTOR(S) | : Thomas Haemmerle et al. | |

It is certified that error appears in the above-identified patent and that said Letters Patent is hereby corrected as shown below:

On the Title Page:
Please correct the Abstract, section 57, as indicated below:

In line 4 of the Abstract, delete "*mycoplasma*" and insert --mycoplasma--

In the Claims:
In Claim 1, column 9, line 26, delete "rTth-pol" and insert --r*Tth*-pol--

In Claim 8, column 10, line 5, delete "*mycoplasma*" and insert --mycoplasma--

In Claim 10, column 10, line 12, delete "*mycoplasma*" and insert --mycoplasma--

In Claim 10, column 10, line 17, delete "*mycoplasma*" and insert --mycoplasma--

In Claim 10, column 10, line 23, delete "*mycoplasma*" and insert --mycoplasma--

In Claim 10, column 10, line 26, delete "rTTh-pol" and insert --r*TTh*-pol--

In Claim 14, column 10, line 34, delete "*mycoplasma*" and insert --mycoplasma--

Signed and Sealed this
Nineteenth Day of March, 2013

Teresa Stanek Rea
*Acting Director of the United States Patent and Trademark Office*